US008608750B2

(12) United States Patent
Faccioli et al.

(10) Patent No.: US 8,608,750 B2
(45) Date of Patent: Dec. 17, 2013

(54) SURGICAL DEVICE FOR INJECTING CEMENT IN A BONE CAVITY

(75) Inventors: Giovanni Faccioli, Monzambano (IT); Renzo Soffiatti, Nogara (IT)

(73) Assignee: Tecres S.p.A., Sommacampagna (Verona) (IT)

( * ) Notice: Subject to any disclaimer, the term of this patent is extended or adjusted under 35 U.S.C. 154(b) by 94 days.

(21) Appl. No.: 12/756,637

(22) Filed: Apr. 8, 2010

(65) Prior Publication Data
US 2010/0262151 A1 Oct. 14, 2010

Related U.S. Application Data

(60) Provisional application No. 61/168,295, filed on Apr. 10, 2009.

(51) Int. Cl.
*A61B 17/56* (2006.01)
(52) U.S. Cl.
USPC .............. 606/94; 604/248; 604/256; 606/108

(58) Field of Classification Search
USPC ................. 606/108, 92–94; 604/248, 256, 604/533–539; 433/80, 88
See application file for complete search history.

(56) References Cited

U.S. PATENT DOCUMENTS

| 7,112,205 | B2 * | 9/2006 | Carrison ................. 606/92 |
| 7,798,209 | B1 * | 9/2010 | Robichaux et al. ......... 166/84.1 |
| 2007/0272403 | A1 * | 11/2007 | Robichaux et al. ......... 166/85.1 |

* cited by examiner

*Primary Examiner* — Todd Manahan
*Assistant Examiner* — Jessica Weiss
(74) *Attorney, Agent, or Firm* — Tutunjian & Bitetto, P.C.

(57) ABSTRACT

A surgical device and method for injecting cement in a bone cavity includes an elongated, hollow body to be inserted partially into the cavity. The body has an inner lumen with a distal opening to expel cement therefrom. An entry plug for the cement is connected to a cement pressurized supply. The entry plug is in fluid communication with the lumen to deliver cement through the entry plug, wherein the entry plug is movably mounted on the hollow body.

20 Claims, 4 Drawing Sheets

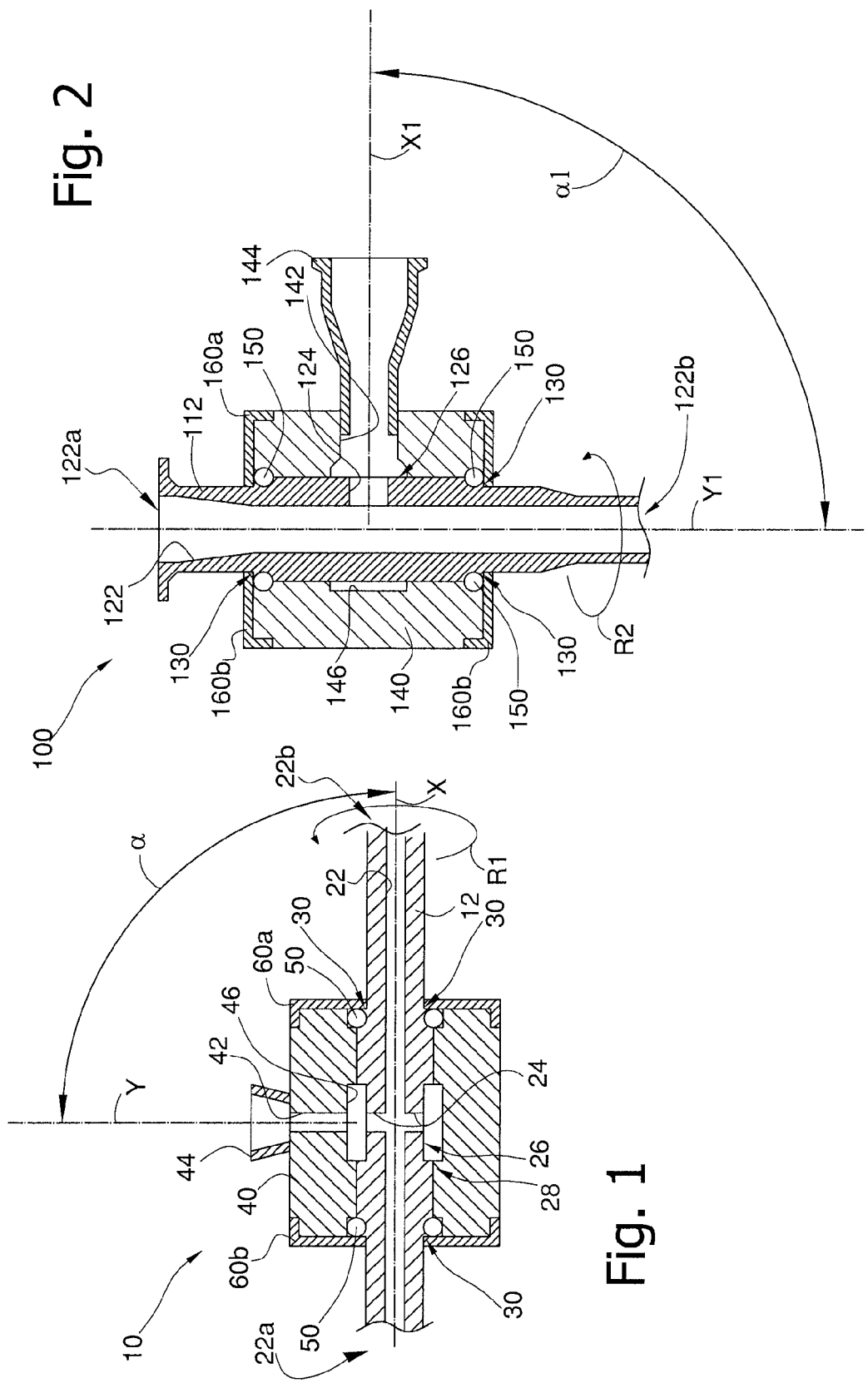

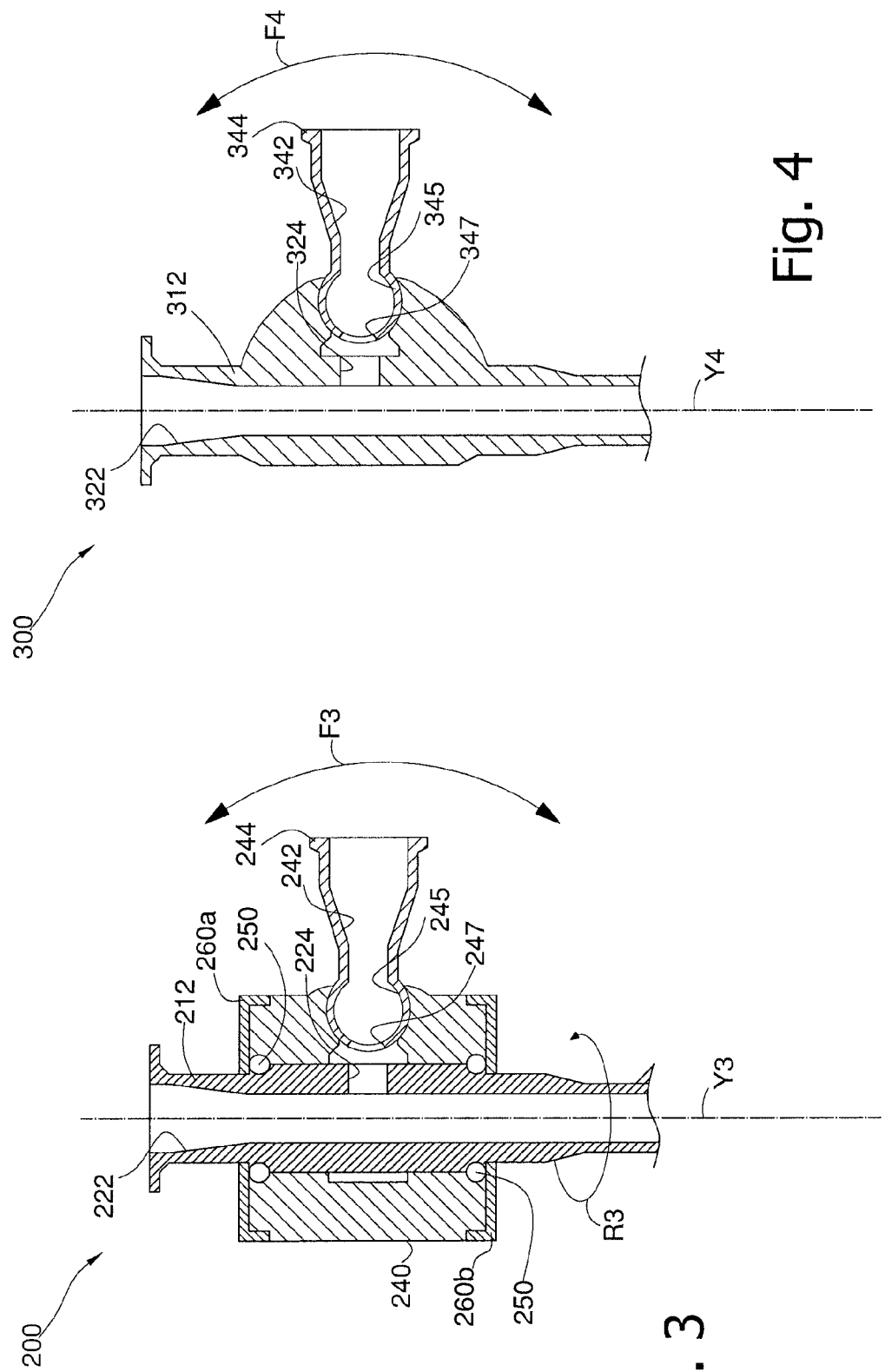

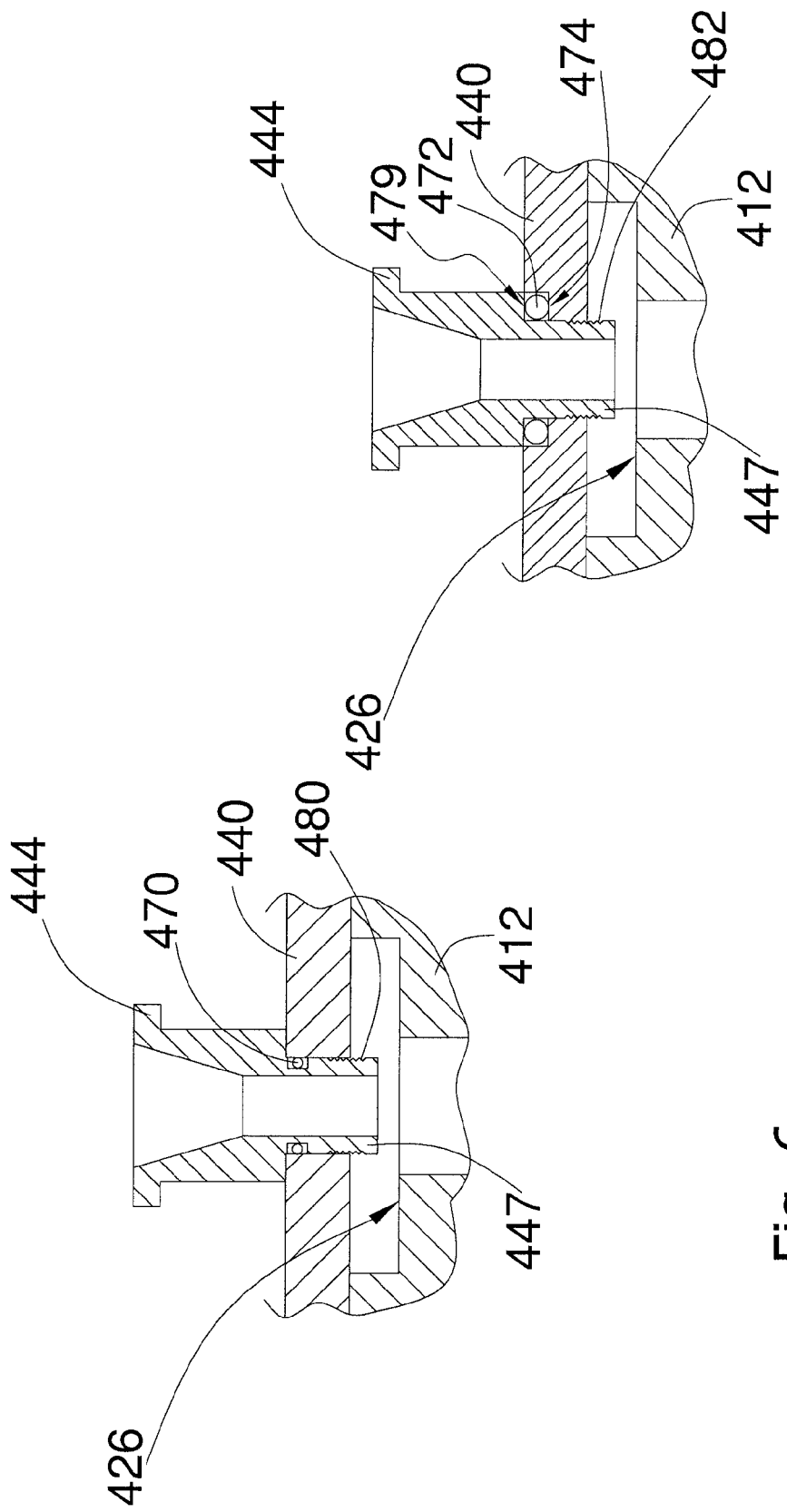

SURGICAL DEVICE FOR INJECTING CEMENT IN A BONE CAVITY

CROSS-REFERENCE TO RELATED APPLICATIONS

This application claims the benefit of U.S. Provisional Application Ser. No. 61/168,295, filed Apr. 10, 2009, which is incorporated by reference herein in its entirety.

BACKGROUND

1. Technical Field

The present invention relates to surgical devices and more particularly to a surgical device for injecting cement in a bone cavity.

2. Description of the Related Art

In surgery, particularly in osteoplasty or vertebroplasty, cement delivery devices are known which are adapted to allow an operator to inject viscous cement inside the vertebral body. These devices, hereby referred to as an example, provide control over the exact deposit location and directionality of cement delivery by means of a curvable, distal delivery needle, which allows navigation within the vertebral body. As a result of the needle design, the operator at all times has control over the curvature and direction of the delivery needle, providing direct access to the entire vertebral body, which allows for patient specific customization of cement delivery during the procedure.

A main drawback of such devices stems from the necessity for the operator to rotate the needle inside the vertebral body in order to spread the cement uniformly therein. In fact, the needle is able to bend only moving inside a plane (like the movement of a finger). Therefore, to direct the injected cement in all directions the needle must be rotated.

Since the cement is supplied to the needle through a pipe connected fixedly to the same needle, usually at a right angle, the operator must change position around the patient to rotate the needle. In a surgery room, filled with machines and operating personnel, this may be unpractical, awkward or even impossible.

SUMMARY

In useful embodiments, surgical operation of the foregoing type is eased by allowing a greater freedom of movement to a surgeon. This may be achieved by a surgical device for injecting cement in a bone cavity, comprising an elongated, hollow body to be inserted partially into the cavity; the body having an inner lumen with a distal opening to expel cement therefrom; an entry plug for the cement from a cement pressurized supply the entry plug being in fluid communication with the lumen to deliver cement through it, wherein the entry plug is mounted movably on the hollow body.

The mobile disposition of the plug on the hollow body, whether it has an inner lumen with only an outlet for the cement or with another opposite inlet from which the inside of the bone may be reached, allows the plug or a connector for the cement from the device to be free, making it much more handy and efficient. The pipe conveying cement to the device may articulate and/or have a joint on it, thereby eliminating the drawbacks described. Advantageous variants of the invention are also provided. A surgical device and method for injecting cement in a bone cavity includes an elongated, hollow body to be inserted partially into the cavity. The body has an inner lumen with a distal opening to expel cement therefrom. An entry plug for the cement is connected to a cement pressurized supply. The entry plug is in fluid communication with the lumen to deliver cement through the entry plug, wherein the entry plug is movably mounted on the hollow body.

These and other features and advantages will become apparent from the following detailed description of illustrative embodiments thereof, which is to be read in connection with the accompanying drawings.

BRIEF DESCRIPTION OF DRAWINGS

The advantages of the invention will be clearer from the following description of embodiments thereof, with the attached drawings wherein:

FIG. 1 shows a cross sectional view of a first variant of the invention;

FIG. 2 shows a cross sectional view of a second variant of the invention;

FIG. 3 shows a cross sectional view of a third variant of the invention;

FIG. 4 shows a cross sectional view of a fourth variant of the invention;

FIG. 6 shows a cross sectional view of a detail in FIG. 5; and

FIG. 7 shows a cross sectional view of a variant for the detail in FIG. 6.

DETAILED DESCRIPTION OF PREFERRED EMBODIMENTS

Figure 5:
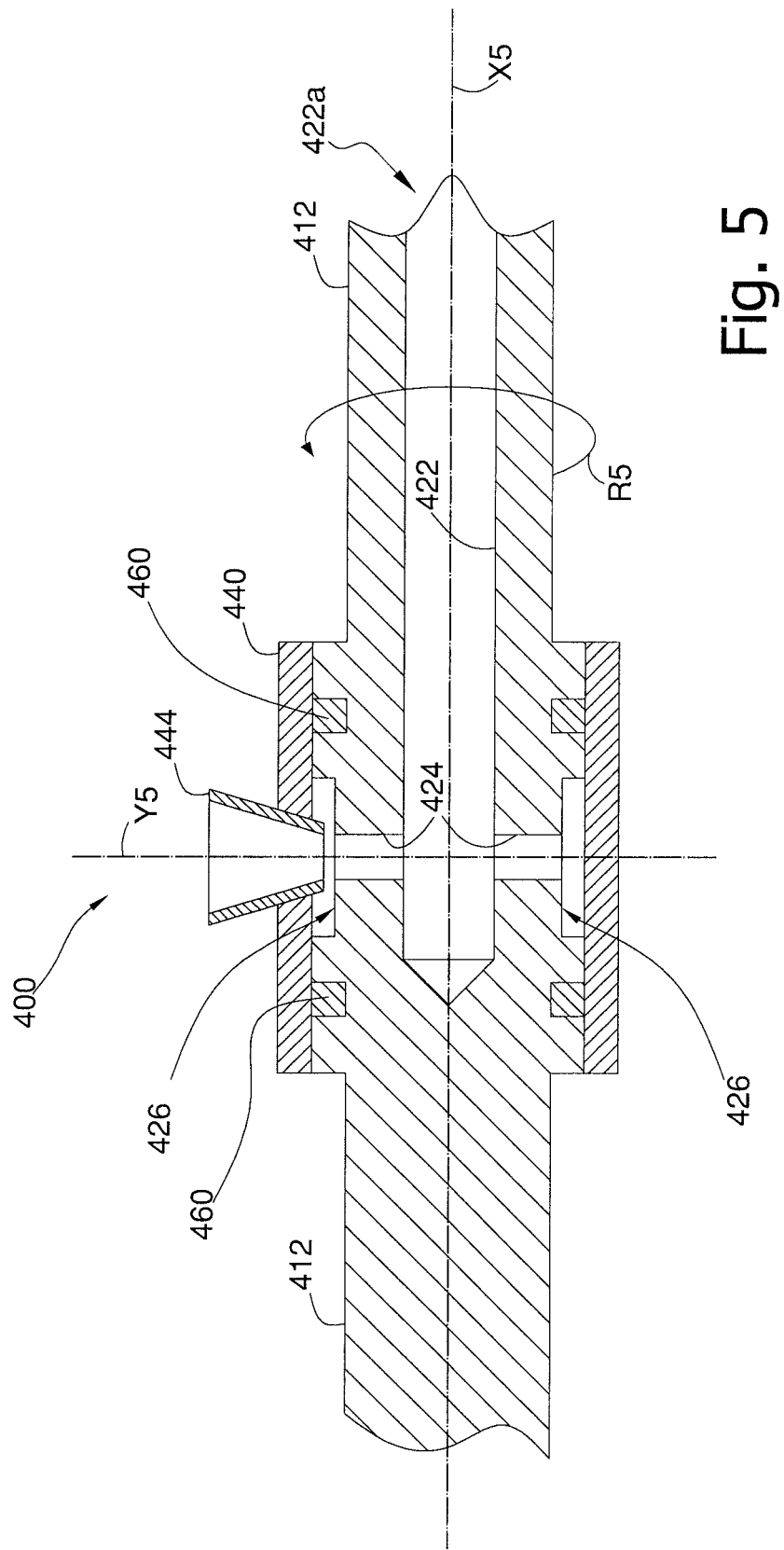
FIG. 5 shows a cross sectional view of a fifth variant of the invention.

A surgical device for injecting cement in a bone cavity is provided. In one embodiment, the device includes an elongated, hollow body to be inserted partially into the bone cavity. The body includes an inner lumen with a distal opening to expel cement therefrom, and an entry plug for the cement from a cement pressurized supply. The entry plug is in fluid communication with the lumen to deliver cement through it, wherein the entry plug is mounted movably on the hollow body. The mobile disposition of the plug on the hollow body, whether it has an inner lumen with only an outlet for the cement or with another opposite inlet from which the inside of the bone may be reached, allows the plug or a connector for the cement from the device to be free, making it much more handy and efficient. The pipe conveying cement to the device may articulate and/or have a joint on it for flexible operation.

Referring now to the drawings in which like numerals represent the same or similar elements and initially to FIG. 1, a first device according to the invention is indicated at 10 and comprises a tubular body 12 elongated along a longitudinal axis X. The body 12 has a coaxial inner channel 22 with an inlet 22a and an outlet 22b. The channel 22 communicates radially (along an axis Y orthogonal to axis X, see angle α) with two orthogonal channels 24 opening into an annular recessed portion 26. The recessed portion 26 is obtained in a thicker region 28 of the body 12, wherein the region 28 forms a circular step 30 with the remaining part of the body 12. The body 12 in this example may be a steerable needle to inject cement in a bone.

An annular member 40 is arranged around the body 12 and has a radial, pass-through channel 42 terminating externally with a funnel-shaped connector 44. The channel 42 opens into an annular, inner recessed portion 46 arranged over and matching in width the recessed portion 26. The innermost radius of the member 40 matches very precisely the outermost radius of the region 28 to have a good fitting. Two fluid-tight ring gaskets 50 are arranged between the annular member 40 and the body 12 into proper recessed seats. The gaskets 50 are placed at the borders of the region 28, opposite to the portion 26.

Two calotte-shaped covers 60a, 60b are attached, e.g. by means of ultrasonic welding, to the sides of the annular member 40, so as to enclose the gaskets 50 therebetween and to abut against a step 30. In this manner the covers 60a, 60b retain the member 40 in a fixed position with respect to the axis X over the body 12. The annular member 40 and the covers 60a, 60b result in being integral with each other and are able to be rotated on the body 12 about the axis X in a fluid-tight manner, but without asking for an excessive driving torque. These two elements slide over the gaskets 50. Also, it is to be noted that the device 10 is symmetric with respect to axes X and Y.

During surgery operations, the inlet 22a is used to control a wire (not shown) running inside the channel 22 up to the body 12's tip (not shown), where it can pull the end thereof to bend it. The connector 44 is connected by a pipe to a pump supplying cement. The cement enters the connector 44, runs into the channels 24 and invades the regions 26, 46, from which it goes on inside the channel 22 towards the outlet 22b to the bone. Since the connection carrying the cement is not fixed to, but can rotate on, the body 12 thanks to the rotation of the member 40, it is apparent that the available movements of a surgeon are greatly improved. The body 12 can be rotated about the axis X (see arrow R1), e.g. to better distribute the cement inside a vertebra, without the constraint of moving the cement supplying pipe. Instead, the member 40 rotates around the body 12 and leaves the cement entry point in a quite constant position.

FIG. 2 relates to a variant of the device, indicated by 100. The second variant comprises a tubular, tapered body 112 elongated along a longitudinal axis Y1. The body 112 has a coaxial inner channel 122 with a funnel-shaped inlet 122a and an outlet 122b. The channel 122 communicates radially (along an axis X1 orthogonal to axis Y1, see angle α1) with one or more channels 124 opening in the lateral surface 126 of the body 112.

An annular member 140 is arranged around the body 112 and has a radial, pass-through channel 142 terminating externally with a funnel-shaped connector 144 fixed thereto. The channel 142 opens into an annular, inner recessed portion 146 of the member 140. The innermost radius of the member 140 matches very precisely the outer most radius of the body 112, to have a good fitting. Two fluid-tight ring gaskets 150 are arranged between the annular member 140 and the body 112 into proper recessed seats. The gaskets 150 are placed at a distance from, and beside, the portion 146 and the channel 142.

Two calotte-shaped covers 160a, 160b are attached, e.g., by means of ultrasonic welding, to the sides of the annular member 140, so as to enclose the gaskets 150 therebetween and to abut against a step 130. In this manner the covers 160a, 160b retain the member 140 in a fixed position with respect to the axis Y1 over the body 112.

The annular member 140 and the covers 160a, 160b result in being integral with each other and are able to be easily rotated on the body 112 about the axis Y1 in a fluid-tight manner. These two elements slide over the gaskets 150. It is to be noted that the device 100 is symmetric with respect to axes X1 and Y1.

During surgery operations, the operation of the device 100 is analogous to that of device 10 as to the free rotation of the member 140 on the body 112, thereby allowing the movement of the cement entry point on the body 112 (see arrow R2). The difference in this variant is that the inlet 122a may be used to insert in a bone cavity to be cemented to an IR antenna to kill cancer, a micro-camera or any other device able to explore, or operate inside, such bone cavity.

FIG. 3 shows a third variant, indicated by 200; the central part being identical to the device 100, thus it will be described briefly. The third variant comprises a tubular body 212, elongated along a longitudinal axis Y3, having a coaxial inner channel 222. The channel 222 communicates radially with one or more channels 224 opening in the lateral surface thereof.

An annular member 240, analogous to member 140, is arranged around the body 212. The member 240 houses inside, in a spherical cavity, a spherical termination 245 of a connector 244. The connector 244 is hollow and exhibits an inner channel 242 opening both outwards and toward the spherical termination 245, which has an opening 247 communicating with the channel 224. As before, two fluid-tight ring gaskets 250 are arranged between the annular member 240 and the body 212, thereby promoting the rotatable coupling thereof.

Two calotte-shaped covers 260a, 260b are attached to the sides of the annular member 240, so as to enclose the gaskets 150 therebetween. The annular member 240 is able to be easily rotated on the body 212 about the axis Y3 in a fluid-tight manner (see arrow R3). Also, the connector 244 can be oriented with respect to the member 240 gaining an additional degree of freedom (see arrow F3).

During surgery operations, the operation of the device 200 is analogous to that of device 100, with the benefit that the pipe carrying cement, to be connected to the connector 244, has also an articulated connection on the member 240, and hence the device 200 is more maneuverable.

Another variant 300 of the device is shown in FIG. 4. This variant comprises a tubular body 312 elongated along a longitudinal axis Y4. The body 312 has a coaxial inner channel 322 communicating radially with one or more channels 324 opening toward a spherical cavity 347 of a spherical termination 345 belonging to a connector 344. The connector 344 is hollow and exhibits an inner channel 342 opening both outwards and toward the spherical termination 345, which, through the opening 347, makes the channel 324 communicate with the mouth of the connector 344.

Thanks to its spherical termination 345 the connector 344 can be oriented jointly with respect to the body 312 gaining an additional degree of freedom (see arrow F4) for the connector 344. Thus, during surgery operations, the device 300 has the benefit that the pipe carrying cement has also an articulated connection on the body 312. Even if with minor amount with respect to the previous one, the device 300 is more maneuverable than the known devices.

Another device according to the invention is shown at 400 in FIG. 5 and comprises a tubular body 412 elongated along a longitudinal axis X5, in one example, a needle for injecting cement. The needle 412 has a coaxial, inner channel 422 with an outlet 422a. The channel 422 communicates radially (along an axis Y5 orthogonal to axis X5) with two orthogonal channels 424 opening into an annular recessed portion 426. The recessed portion 426 can be obtained by milling the needle 412.

An annular member 440 is arranged around the body 412 and has a funnel-shaped external connector 444 whose tip projects internally from the inner wall of the member 440. The innermost radius of the member 440 matches very precisely the outermost radius of the needle 412, in order to have a good fitting. Two fluid-tight ring gaskets 460 are arranged between the annular member 440 and the needle 412 into proper recessed seats. The member 440 can rotate about the axis X5 on the needle 412 and can also slide thereon for a distance longitudinally along the axis X5. This is because the tip of the connector 444 can move between the walls of the annular recessed portion 426 without coming out therefrom, sliding on the gaskets 460.

During surgery operations, the left part (in the drawing) of the needle 412 with respect to the member 440 can be used to control or handle the needle 412. The operation of the device 400 is analogous to that of device 100 as to the free rotation of the member 440 on the needle 412, thereby allowing in such a manner the movement of the entry plug for the cement on the needle 412 (see arrow R5).

FIGS. 6 and 7 show two different methods for fixing the connector 444 to the member 440. This holds also for the preceding and other variants. In FIG. 6 the connector 444 exhibits on a stem 447 thereof, a terminal thread 480 to be threaded on a corresponding thread in the member 440. On the stem 447, in a more external position, there is obtained a circular seat to house a fluid-tight gasket 470 into it.

In FIG. 7 the connector 444 still exhibits on a stem 447 thereof, a terminal thread 482 to be threaded on a corresponding thread in the member 440. On the stem 447, in a more external position and flush to the surface of the member 440, there is obtained an undercut 479. Between the undercut 479 and a circular-plan step 474 obtained on the surface of the member 440 there is housed a fluid-tight gasket 472.

Essentially, with respect to FIG. 6 the way the gasket 470 is integrated in the device is modified. Generally speaking, the covers 60a, 60b or 160a, 160b or 260a, 260b may also be fixed by screwing to a thread portion in the member 40, 140, 240 or by gluing. Suitable materials for such covers include, e.g., polycarbonate or nylon. The gaskets 50, 150, 250, 460 470, 472 may be of different type, e.g., o-rings or lip-gaskets.

Having described preferred embodiments of a device and methods for its use (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A surgical device injecting bone cement in a bone cavity, comprising:
   an elongated, hollow body to be inserted partially into the bone cavity; the body having an inner lumen with a distal opening to expel bone cement therefrom;
   a member having access to the cement from a bone cement pressurized supply, the member being in fluid communication with the lumen to deliver bone cement through the hollow body, wherein the member is movably mounted on the hollow body; and
   further comprising two cover elements coaxially applied to the member and fixed thereto on opposite sides, the cover elements abutting on annular steps formed on a lateral outer surface of the body so as to enclose and constrain the member between them.

2. The device according to claim 1, wherein the member is rotatably mounted in a coaxial manner about a longitudinal axis of the body.

3. The device according to claim 1, wherein the body further comprises an opening for gaining access to the cavity through the lumen and located opposite from the distal opening.

4. The device according to claim 3, wherein the member comprises a rotatable member rotatably mounted around the lateral surface of the body, the rotatable member being provided with a connector for a pipe for the bone cement and with at least one pass-through, radial channel allowing bone cement fluid communication with the lumen of the body.

5. The device according to claim 4, wherein the body comprises at least one radial channel connecting its lateral surface to the lumen and located so as to receive the bone cement coming from a pass-through, radial channel of the rotatable member.

6. The device according to claim 5, wherein the at least one radial channel of the body and the at least one pass-through, radial channel of the rotatable member have parallel axes.

7. The device according to claim 6, wherein the rotatable member has an annular, recessed portion at an outlet of the at least one pass-through, radial channel, said portion facing the lateral surface of the body.

8. The device according to claim 7, wherein the body in its lateral surface has an annular, recessed portion at the outlet of the at least one radial channel.

9. The device according to claim 1, wherein the two cover elements form a fluid-tight slidable seal with respect to the body.

10. The device according to claim 4, wherein one or more fluid-tight gaskets are arranged between the rotatable member and the body for avoiding bone cement leaks.

11. The device according to claim 1, wherein the member is mounted through a joint on the body and with respect to the body.

12. The device according to claim 4, wherein the connector is mounted through a joint on the rotatable member.

13. The device according to claim 4, wherein the connector is fixed in the rotatable member through a coupling of a threaded portion thereof.

14. The device according to claim 13, wherein at the threaded portion there is mounted a gasket placed between the connector and the rotatable member.

15. The device according to claim 14, wherein the gasket placed between the connector and the rotatable member is housed in a peripheral groove on said connector.

16. The device according to claim 15, wherein the gasket placed between the connector and the rotatable member is placed between a peripheral undercut on said connector and a circular-plan step on said rotatable member.

17. The device according to claim 13, wherein an end of the connector projects internally from the rotatable member and is slidingly confined between the side walls of a groove on the lateral surface of the body.

18. A surgical device injecting bone cement in a bone cavity, comprising:
   an elongated, hollow body to be inserted partially into the bone cavity, the body having an inner lumen with a distal opening to expel bone cement therefrom, and including a thicker region having at least two recessed seats;
   a movable member having access to the bone cement from a bone cement pressurized supply, the movable member being in fluid communication with the lumen to deliver bone cement through the hollow body, wherein the movable member is rotatably mounted to and forms a fluid-tight slidable seal with a surface of the hollow body; and
   at least two gaskets disposed in and completely filling the recessed seats of the thicker region, wherein an innermost radius of the movable member matches an outermost radius of the elongate body to form the fluid-tight slidable seal enabling the movable member to rotate about a longitudinal axis of the body and to slide along said longitudinal axis.

19. The device of claim 18, wherein the member includes a connector having a tip projecting internally into an inner wall of the movable member.

20. The device of claim 19, wherein the body includes an annular recessed portion and wherein the tip projects into said annular recessed portion.

* * * * *